(12) United States Patent
Utsugi

(10) Patent No.: US 7,183,455 B2
(45) Date of Patent: Feb. 27, 2007

(54) ADHESIVE DRESSING

(75) Inventor: Ryuichi Utsugi, Tokyo (JP)

(73) Assignee: DRDC Limited, Tokyo (JP)

( * ) Notice: Subject to any disclaimer, the term of this patent is extended or adjusted under 35 U.S.C. 154(b) by 395 days.

(21) Appl. No.: 10/228,080

(22) Filed: Aug. 27, 2002

(65) Prior Publication Data

US 2004/0044299 A1     Mar. 4, 2004

(51) Int. Cl.
*A61F 13/00*     (2006.01)
(52) U.S. Cl. .................................................... 602/58
(58) Field of Classification Search ............... 604/360, 604/361, 385.01, 304–308; 602/41–59; 128/888, 128/889; 424/443–449
See application file for complete search history.

(56) References Cited

U.S. PATENT DOCUMENTS

| | | | | |
|---|---|---|---|---|
| 4,070,912 A * | 1/1978 | McNaughtan et al. | ...... | 374/162 |
| 4,651,749 A * | 3/1987 | Sagi | ...... | 600/549 |
| 4,738,674 A * | 4/1988 | Todd et al. | ...... | 604/361 |
| 4,813,942 A * | 3/1989 | Alvarez | ...... | 602/49 |
| 5,109,874 A * | 5/1992 | Bellingham et al. | ...... | 128/888 |
| 5,181,905 A * | 1/1993 | Flam | ...... | 602/41 |
| 6,235,964 B1 * | 5/2001 | Kadash et al. | ...... | 602/41 |
| 6,322,750 B1 * | 11/2001 | Barclay | ...... | 422/56 |
| 6,589,779 B1 * | 7/2003 | McDevitt et al. | ...... | 435/288.7 |
| 6,617,488 B1 * | 9/2003 | Springer et al. | ...... | 604/361 |

* cited by examiner

*Primary Examiner*—Henry Bennett
*Assistant Examiner*—Adam Brandt
(74) *Attorney, Agent, or Firm*—Michael Bednarek; Paul, Hastings, Janofsky & Walker LLP

(57) ABSTRACT

To provide an adhesive dressing that allows a wearer to determine growth of bacteria, if any, as early as possible when the adhesive dressing is staying on the skin of the wearer for wound healing. The adhesive dressing includes a see-through backing made of a silicone material and four circular keepers provided on one surface of the backing. The keepers are impregnated with chemical compositions that change in color to the extent that the color change is visible to the naked eye when bacteria in a wound grow. The conditions to trigger the color change varies from composition to composition. An adhesive is applied along the periphery of the backing. When bacteria grow in the wound, the change in color of the chemical compositions impregnated in the keepers can be visually checked through the backing. This contributes to prompt and early treatment of infected wounds.

28 Claims, 2 Drawing Sheets

ADHESIVE DRESSING

BACKGROUND OF THE INVENTION

The present invention relates to an adhesive dressing for medical purposes, such as wound dressings, bandage strips, and surgical tapes.

Adhesive dressings are widely used in various clinical services in the form of bandage strips or other dressings. For example, adhesive dressings are used to treat wounds including blisters, cuts, scratches, and burn injuries. More recent treatments for laser burns also employ adhesive dressings. Such adhesive dressings typically comprise a backing, and an adhesive layer on the surface of the backing that is to be brought into contact with the skin of a person. Typical conventional backings for adhesive dressings are made of a non-transparent material. This means that the condition of a wound under a dressing cannot be visually checked while the dressing is staying on the skin. Accordingly, a wound may be aggravated under the dressing if bacteria grow in the wound before it heals. In this invention, the word "bacterium" contains virus and microorganism it is supposed that it will not be bacterium if a definition is generally given.

In order to avoid deterioration of the wound, an adhesive dressing may frequently be removed for medical attention to be received. However, some situations do not allow for frequent removal of the dressings. This is particularly true when occlusive or wet dressings are applied. When an occlusive or wet dressing is used, the area under treatment is completely covered with the dressing. The area is kept until the wound has healed. The wound is placed in contact with body fluid during this healing period. Wounds have traditionally been covered with dry dressings such as gauze. Occlusive dressings and wet dressings, on the other hand, have attracted a lot of attention as an approach that can enhance the healing process and reduce healing time. The wet dressings have a potential of reducing healing time. However, if a wound is infected with bacteria, they are more likely to grow. The growth of the bacteria, if any, should be identified as early as possible. The wound should be cleaned, disinfected, and dressed with a sterile adhesive dressing. To this end, the adhesive dressing may be removed in certain intervals to check the condition of the wound. However, this often takes some work. In other words, it is more advantageous to avoid unnecessary removal of dressings and treatment of wounds, and cover the area under treatment for a longer period of time for helping a wound to heal.

Therefore, an object of the present invention is to provide an adhesive dressing that allows a wearer to determine growth of bacteria, if any, as early as possible when the adhesive dressing is staying on the skin of the wearer for wound healing.

SUMMARY OF THE INVENTION

The present inventor undertook thorough research to obtain such adhesive dressings. As a result, the present invention was thus accomplished.

More specifically, the present invention provides an adhesive dressing designed to be placed over a wound, comprising: a backing having a first surface and a second surface opposite the first surface; an adhesive layer provided on at least a part of the first surface of the backing to secure the adhesive dressing to the skin of a person or an animal with the first surface facing the skin; and a chemical composition applied to the first surface of the backing, the adhesive layer changing in color to the extent that the color change is visible to the naked eye through the backing when bacteria grow in the wound.

Alternatively, the present invention provides an adhesive dressing designed to be placed over a wound, comprising: a backing having a first surface and a second surface opposite the first surface, the backing being made of an absorbent or water-permeable material; an adhesive layer provided on the first surface of the backing to secure the adhesive dressing to the skin of a person or an animal with the first surface facing the skin; and a chemical composition impregnated in the backing, the chemical composition changing in color to the extent that the color change is visible to the naked eye when bacteria grow in the wound.

These adhesive dressings are stuck to the skin to use. In the former adhesive dressing, the chemical composition on the wound changes in color when bacteria grow in the wound while the dressing is staying on the skin. The color change is visible through the backing. In the latter adhesive dressing, the chemical composition impregnated in the backing and brought into contact with exudate changes in color when bacteria grow in the wound. The color change is visible to the naked eye as the color change of the backing.

By using the adhesive dressing of the present invention, a person who has no special expertise in medical treatments can properly identify the growth of bacteria, if any, in a wound. When color change is observed, the person can easily clean, disinfect and dress the wound with a sterile adhesive dressing. This allows prompt treatment for infected wounds.

This indicates that there is little possibility of wound infection unless the color of the chemical composition does not change. Adhesive dressings may be kept over the area under for a longer period of time, wherever possible.

The backing of the present invention may be any backing as long as any change in color of the chemical composition is visible through the backing while the dressing is staying on the skin. For example, the backing may be formed of a colorless transparent, colored transparent, translucent, semi-transparent, or even clear-colored material. In addition, the backing may be formed as a sheer mesh of a non-transparent or opaque material. What is required for the backing is that the color change is visible through the backing.

The backing according to the former aspect of the present invention may be water-permeable or water-impermeable. When the backing is water-impermeable, the resulting adhesive dressings are suitable as wet dressings.

The backing according to the former aspect of the present invention may be made of any one of suitable materials as long as the color change in color of the chemical composition can visually be checked through the backing. For example, the backing may be made of a resin material. Resins may be used to provide transparent, translucent, or water-impermeable backings.

The backing according to a latter aspect of the present invention may be made of any absorbent or water-permeable materials. Of course, an absorbent and water-permeable backing may be used. Materials of the backing are not specifically limited as long as the above-mentioned requirements are satisfied. However, fabric (woven fabric and non-woven fabric) or paper may suitably be used.

The chemical composition indicates the growth of bacteria, if any, by means of change in color to the extent that the color change is visible to the naked eye. In the former aspect of the present invention, the chemical composition is provided on at least a part of the surface of the skin to be brought into contact with the skin. The chemical composition may be provided over a different range from the adhesive layer. Alternatively, the chemical composition may be incorporated into the adhesive layer. The surface of the backing to be opposed to the skin (contact surface) may be provided with keeper to keep the chemical composition. In such a case, the chemical composition is impregnated in the keeper on the contact surface of the backing.

On the other hand, the chemical composition according to the latter aspect of the present invention is impregnated in the backing. In such a case, the chemical composition may be impregnated in the entire backing or only in a predetermined area of the backing.

The chemical composition according to the present invention may be a single composition or may include different compositions that change in color under different conditions. In the latter case, the chemical composition may be a combination of pH indicators, hydrogen sulfide indicators or other chemical compositions described below.

In the present invention, two or more kinds of chemical compositions may be incorporated into the adhesive layer at different locations. Alternatively, these chemical compositions may be impregnated in the keeper or in the backing at different locations. The chemical composition(s) according to the present invention may be any one of suitable compositions that change in color to the extent that the color change is visible to the naked eye when bacteria grow in the wound.

For example, the chemical indicator of the present invention may be a pH indicator that changes in color to the extent that the color change is visible to the naked eye when the chemical composition varies from neutral to acidic. This chemical composition is based on the fact that human body fluids are naturally maintained at about neutral pH but shift to acidic as bacteria grow. The pH indicator is not specifically limited. Any one of appropriate compositions may be used that exhibits different colors between the acidic and neutral pHs to the extent that the color change is visible to the naked eye.

More specifically, the pH indicator of the present invention may be selected from the group consisting of Indigo Carmine, Nile Blue, Methyl Red, Phenolphthalein, Congo Red, Bromcresol Green, Bromphenol Red, Bromthymol Blue, Cresol Red, Thymol Blue, Bromphenol Blue, Tetrabromphenol Red, Bromcresol Purple, Alizarin Yellow, Aniline Blue, Litmus, Andrade, Neutral Red. Alternatively, two or more of them may be combined.

Chemical compositions that exhibit different colors between a pH value of equal to or larger than 3 and a pH value of equal to or smaller than 3, to the extent that the color change is visible to the naked eye, can indicate the growth of bacteria more precisely. For example, Thymol Blue, Phenol Blue, and Phenol Red may be used for such purposes.

Besides or in addition to the pH indicator, a hydrogen sulfide indicator may also be used for the chemical composition of the present invention that changes in color to the extent that the color change is visible to the naked eye when the chemical composition reacts with hydrogen sulfide. This chemical composition is based on the fact that hydrogen sulfide is produced during the decomposition of organic matter by bacteria. Examples of the hydrogen sulfide indicator include lead acetate and ferric ions. At least one of them may be used for this purpose. Alternatively, various tests are available to detect or indicate bacteria. Of these, any tests that can exhibit different colors to the extent that the color change is visible to the naked eye in response to the increase in number of bacteria may be used for the chemical compositions of the present invention.

The chemical composition(s) of the present invention may be mixed with an auxiliary agent that is useful to cause the chemical composition(s) to change in color. For example, phenylalanine may be used as the auxiliary agent when the phenylalanine deaminase test is applied. The phenylalanine deaminase test is for demonstrating whether a bacterium can break down the amino acid phenylalanine to phenylpyruvic acid. In such a case, the amino acid phenylalanine that serves as the pH indicator to cause the color change in response to a shift of pH corresponds to the auxiliary chemical composition of the present invention.

Other examples of the tests that can be applied to the present invention include, but not limited to, phosphatase tests, acid fermentation tests, Methylene Blue milk reduction tests, malonate tests, and Litmus milk tests. The phosphatase test is based on the principle that the phosphatase enzyme liberates phenolphthalein from a phenolphthalein diphosphate substrate. With bacteria, phenolphthalein changes from colorless to orange-pink. The phosphatase test is mainly used to determine whether staphylococci or *Escherichia coli* is present. The acid fermentation is to indicate the change in pH to acidic due to metabolites produced by oxidation or fermentation of sugar by bacteria. As the chemical composition, Prussian Blue or Bromcresol Purple is used. The Methylene Blue milk reduction test is to determine the amount of bacteria in a medium supplemented with milk. The reaction involves the reduction of Methylene Blue by enzymatic hydrolysis.

DETAILED DESCRIPTION OF THE PREFERRED EMBODIMENTS

Figure 1:
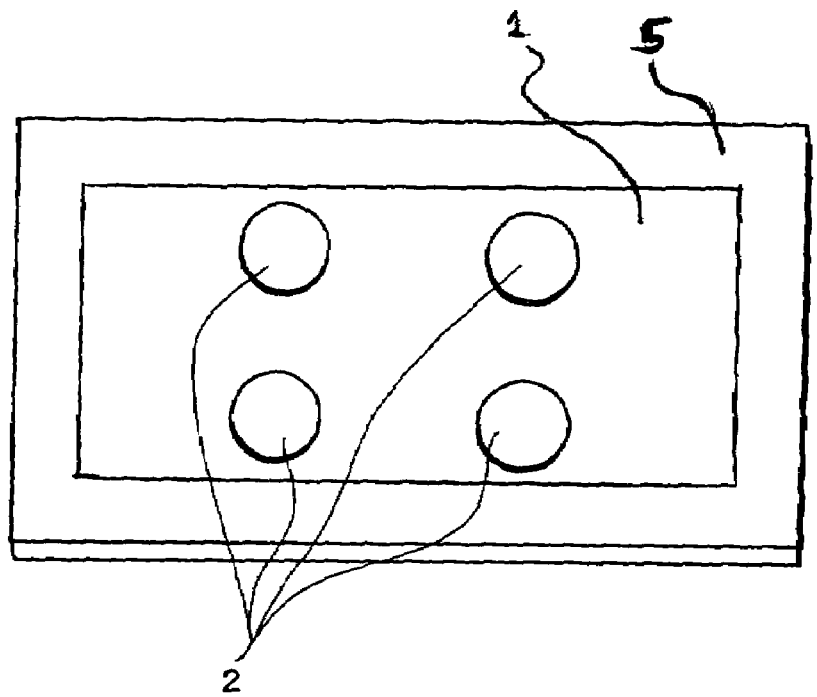
FIG. 1 is a perspective view showing an example of a adhesive dressing according to an embodiment of the present invention.

Adhesive dressings according to first and second preferred embodiments of the present invention are described below.

First Embodiment

An adhesive dressing according to the first embodiment comprises a backing and an adhesive layer. The adhesive layer is provided on the back surface (to be brought into contact with the skin of a wearer) by means of applying an adhesive to the backing at a predetermined location.

The backing of the adhesive dressing according to this embodiment may be colored or colorless transparent, semi-transparent, or translucent. The transparency is such that at least the surface of the skin is visible when the adhesive dressing is staying on the skin. In this embodiment, the backing is colorless transparent.

The backing may be made of one, two or more of various materials. Examples include resins and rubbers such as, but not limited to, silicone, tetron, acrylics, cellophane, fluorocarbon resins, ionomers, nylon, polycarbonate, polyester, polyethylene, polypropylene, polystyrene, polyurethane, polyvinyl alcohol, polyvinylidene chloride, polyvinyl chloride, vinyl acetate, rubber chloride, and vinyl chloride. The backing may be subjected to secondary processing such as coating and corona treatment.

When the adhesive dressing is designed for occlusive dressings or wet dressings, the backing is water-impermeable material. The above-mentioned material(s) may be used to provide occlusive or wet dressings by means of, for example, controlling the thickness of the backing. In this embodiment, silicone or polyurethane is used to form a backing of 0.2 mm in thickness.

The adhesive layer in the adhesive dressing according to this embodiment is required to be applied to the back surface of the backing at a predetermined location or locations. The adhesive layer may be applied over the entire back surface of the backing. Alternatively, the adhesive layer may be applied to the portion of the back surface that is not brought into contact with a wound. The adhesive layer is applied to the entire back surface of the backing.

The adhesive for the adhesive layer may be any one of appropriate adhesives that can hold the backing on the surface of the skin of a wearer for a relatively long period of time. The adhesive may be selected from a range of adhesives that do not have adverse effects on the skin. The adhesive may be, for example, "SK dyne MD-1" available from the Soken Chemical & Engineering Co., Ltd., Tokyo, Japan. In addition, an aluminum chelate cross-linking agent "M-5A" may optionally be added.

Any method may be used to form the adhesive layer on the back surface of the backing. For example, transcription may be used. For this purpose, a release liner made of polyethylene laminate may be used. The release liner may be the one obtained by means of, for example, thermally depositing a polyethylene layer of 15 in thick on quality paper and applying a releasing agent based on a silicon resin to the polyethylene layer.

The adhesive contains a chemical composition incorporated therein that changes in color when the number of bacteria in the wound increases, to the extent that the color change is visible to the naked eye. More specifically, the adhesive in this embodiment contains a pH indicator that changes in color to the extent that the color change is visible to the naked eye when the chemical composition varies from neutral (pH=7) to acidic (pH<7). The amount of the pH indicator may be such that the color change is visible to the naked eye and may be determined depending on the type of the pH indicator to be used. Examples of the pH indicator include those that exhibit different colors between the acidic and neutral pHs to the extent that the color change is visible to the naked eye. For example, Bromthymol Blue may be used as a pH indicator. Alternatively, the pH indicator may be a substance that changes in color at a pH value of about 3.5 to the extent that the color change is visible to the naked eye. That is, the boundary line which the change of the color of the pH indicator produces is in the neighborhood of pH 3.5. The pH indicator may be a substance that differentiates by color between a pH value of about 2 and a pH value of about 4, to the extent that the color change is visible to the naked eye. For example, at least one of Thymol Blue and Phenol Blue may be used for such purposes.

An adhesive containing the pH indicator may be applied to the back surface of the backing through the above-mentioned transcription technique. This provides the adhesive layer having the pH indicator incorporated therein on the back surface of the backing.

In place of the pH indicator, the adhesive may contain a hydrogen sulfide indicator that changes in color to the extent that the color change is visible to the naked eye when the chemical composition reacts with hydrogen sulfide. For example, at least one of lead acetate and ferric ions may be incorporated into the adhesive which may then be applied to the back surface of the backing through the transcription.

An auxiliary agent may be contained in the above-mentioned chemical composition(s). For example, phenylalanine which serves as an auxiliary agent may be mixed with Thymol Blue which serves as a pH indicator. In such a case, the phenylalanine deaminase test is performed before the use of the adhesive dressing. In addition, the chemical composition of the present invention may be mixed with an auxiliary agent that is useful to cause the chemical composition to change in color. For example, when the phenylalanine deaminase test is performed, phenylalanine may be used as the auxiliary agent. The phenylalanine deaminase test is for demonstrating whether a bacterium can break down the amino acid phenylalanine to phenylpyruvic acid. In such a case, the amino acid phenylalanine that serves as the pH indicator to cause the color change in response to a shift of pH corresponds to the auxiliary chemical composition of the present invention.

Different chemical compositions may be provided at different locations in the adhesive. For example, a repeated cycle of the transcription process can produce an adhesive having different chemical compositions provided at different locations thereof. The chemical compositions in this embodiment change in color under different conditions. For example, Phenol Blue is provided at one location and a ferric ion is provided at another location.

The adhesive dressing is designed to be put on the skin with the back surface facing to the skin having a wound so that the wound is completely covered with the dressing.

If bacteria grow in the wound, either the pH indicator or the hydrogen sulfide indicator indicates the growth through the change in color thereof. The color change is visible through the backing. The wound can be cleaned, disinfected, and dressed with a sterile adhesive dressing immediately after a wearer is aware of it.

In the first embodiment, the chemical composition is contained in the adhesive that is provided on the contact surface of the backing. Alternatively, the following modification is also contemplated in the present invention. A keeper may be provided on the contact surface of the backing to keep the chemical composition or compositions. The keeper may be impregnated with the chemical composition to hold it therein. For example, paper or fabric may be used for this purpose.

The keeper may be formed into any desirable shape. The keeper or keepers may be provided on the contact surface of the backing at any location(s). For example, the keeper may be provided as shown in FIGS. 1 to 3 which are perspective views of a backing 1 from the perspective of the contact surface.

In the example shown in FIG. 1, the adhesive dressing comprises a rectangular backing 1. Four circular keepers 2 are provided on the contact surface of the backing 1 in a rectangular pattern. The circular keepers 2 are made of a filter paper and are impregnated with a chemical composition that changes in color under different conditions from each other.

Figure 2:
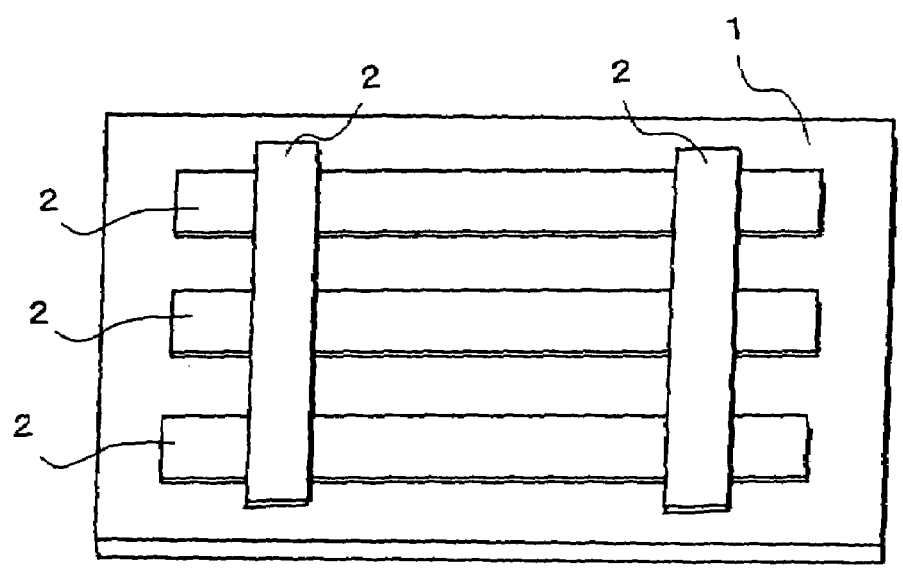
FIG. 2 is a perspective view showing an example of a adhesive dressing according to another embodiment of the present invention.

In the example shown in FIG. 2, the adhesive dressing comprises a rectangular backing 1. Strips of keepers 2 are vertically and horizontally provided on the contact surface of the backing 1. The strip keepers 2 are made of fabric and are impregnated with a chemical composition that changes in color under different conditions from each other.

Figure 3:
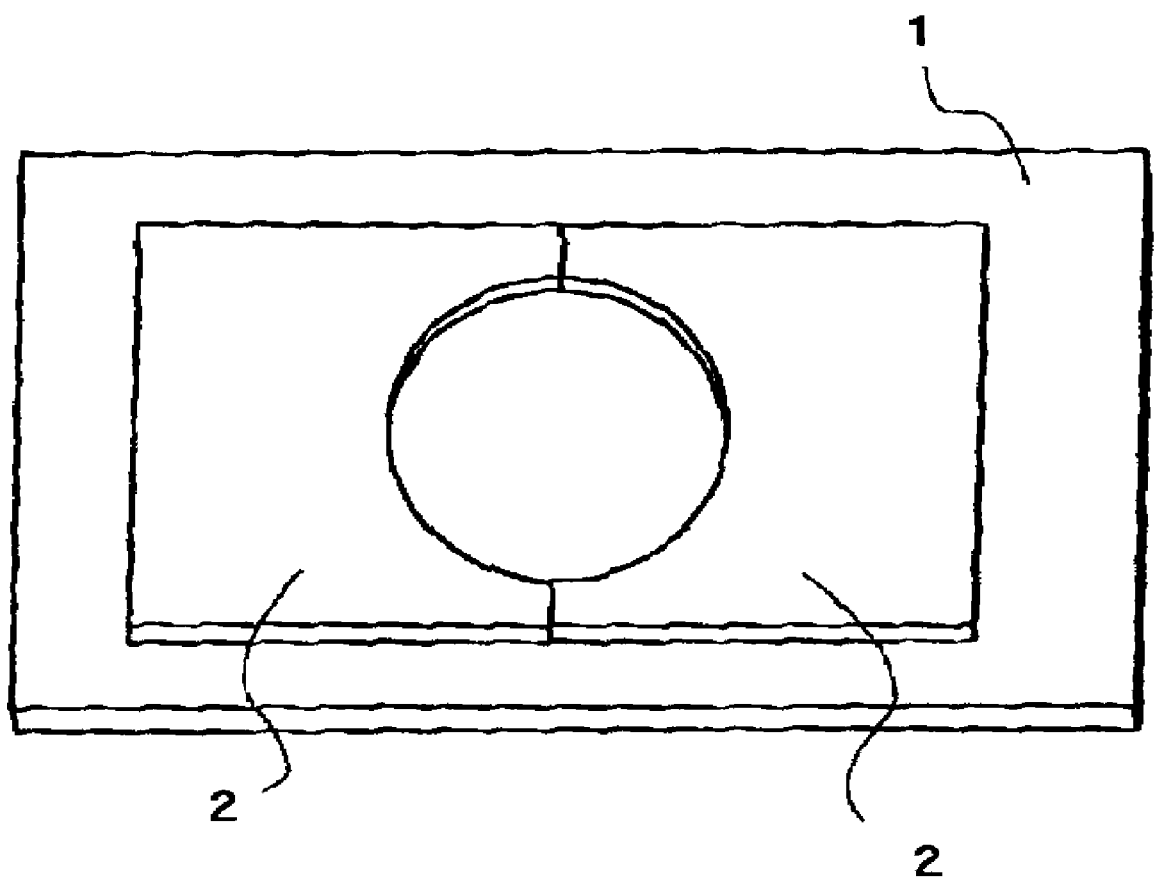
FIG. 3 is a perspective view showing a adhesive dressing according to still another embodiment of the present invention.

In the example shown in FIG. 3, the adhesive dressing comprises a rectangular backing 1. A keeper 2 made of two filter papers is provided on the contact surface of the film backing 1. The keeper 2 has a circular hole formed therein so that the portion of the backing corresponding to the hole is exposed outside. The halves of the keeper 2 are impregnated with a chemical composition that changes in color under different conditions from each other.

An adhesive 5 (as shown in FIG. 1) is applied around the periphery of the adhesive dressings shown in FIGS. 1 to 3 at positions where the backing is exposed outside. The backing 1 shown in FIGS. 1 to 3 as well as the adhesive used are similar to those described above.

Second Embodiment

An adhesive dressing according to this embodiment comprises a backing and an adhesive layer as in the first embodiment. The adhesive layer is provided on the back surface (to be brought into contact with the skin of a wearer) by means of applying an adhesive to the backing at a predetermined location. The second embodiment differs from the first embodiment in the material of the backing.

The backing of the adhesive dressing according to this embodiment is made of a water-permeable and absorbent material such as paper or fabric. More specifically, the backing is made of gauze that is an example of a woven fabric. A transparent resin coating is applied to the surface of the gauze, which may be eliminated when appropriate.

Similar adhesives to those described in conjunction with the first embodiment may be used as the adhesive for the adhesive layer in this embodiment. The adhesive layer in the second embodiment is formed only around the periphery of the backing. Since the transparent resin layer is larger than the gauze and runs off the edge of the gauze. The adhesive layer may be applied only to the back surface of the portion of the resin that runs off the edge of the gauze.

The adhesive for the adhesive dressing according to the second embodiment of the present invention is not required to contain the chemical composition that changes in color to the extent that the color change is visible to the naked eye when the number of bacteria increases. Instead, the chemical composition is impregnated in the gauze that serves as the backing of the adhesive dressing in this embodiment. The chemical composition impregnated in the gauze is similar to those described in conjunction with the first embodiment. In other words, the backing of the adhesive dressing in this embodiment is impregnated with a pH indicator or a hydrogen sulfide indicator. Alternatively, different chemical compositions may be impregnated in the gauze at different locations that change in color under different conditions from each other.

The adhesive dressing according to the second embodiment is also used as in conventionally.

If bacteria grow in a wound, either the pH indicator or the hydrogen sulfide indicator indicates the growth through the change in color thereof. The color change is visible through the backing. The wound can be cleaned, disinfected, and dressed with a sterile adhesive dressing immediately after a wearer is aware of it.

What is claimed is:

1. An adhesive dressing designed to be placed over a wound, comprising:
   a backing having a first surface and a second surface opposite the first surface;
   an adhesive layer provided on at least a part of the first surface of said backing to secure the adhesive dressing to the skin of a person or an animal with the first surface facing the skin; and
   a chemical composition applied within said part of the first surface of said backing, said part is not brought into contact with the wound, and said chemical composition changing in color to the extent that the color change is visible to the naked eye through said backing when bacteria grow in the wound.

2. An adhesive dressing designed to be placed over a wound, comprising:
   a backing having a first surface and a second surface opposite the first surface, said backing being made of an absorbent or water-permeable material;
   an adhesive layer provided on the first surface of said backing to secure the adhesive dressing to the skin of a person or an animal with the first surface facing the skin; and
   a chemical composition impregnated within a part of said backing including said adhesive layer, said part is not brought into contact with the wound, and said chemical composition changing in color to the extent that the color change is visible to the naked eye when bacteria grow in the wound.

3. An adhesive dressing designed to be placed over a wound, comprising:
   a backing having a first surface and a second surface opposite the first surface;
   an adhesive layer provided on at least a first part of the first surface of said backing to secure the adhesive dressing to the skin of a person or an animal with the first surface facing the skin; and
   a chemical composition changing in color to the extent that the color change is visible to the naked eye through said backing when bacteria grow in the wound
   wherein said chemical composition is incorporated into said adhesive layer, and said adhesive layer is not brought into contact with the wound.

4. An adhesive dressing designed to be placed over a wound, comprising:
   a backing having a first surface and a second surface opposite the first surface;
   an adhesive layer provided on at least a first part of the first surface of said backing to secure the adhesive dressing to the skin of a person or an animal with the first surface facing the skin;
   a chemical composition changing in color to the extent that the color change is visible to the naked eye through said backing when bacteria grow in the wound, and
   a keeper provided on the first surface of said backing to keep said chemical composition, said chemical composition being impregnated in said keeper.

5. The adhesive dressing as claimed in claim 1, wherein said chemical composition comprises two or more kinds of chemical compositions that change in color under different conditions.

6. The adhesive dressing as claimed in claim 2, wherein said chemical composition comprises two or more kinds of chemical compositions that change in color under different conditions.

7. The adhesive dressing as claimed in claim 1, wherein said chemical composition is two or more kinds of chemical compositions that change in color under different conditions, the chemical compositions being incorporated into said adhesive layer at different locations.

8. The adhesive dressing as claimed in claim 4, wherein said chemical composition is two or more kinds of chemical compositions that change in color under different conditions, the chemical compositions being impregnated in said keeper at different locations.

9. The adhesive dressing as claimed in claim 2, wherein said chemical composition is two or more kinds of chemical compositions that change in color under different conditions, the chemical compositions being impregnated in said backing at different locations.

10. The adhesive dressing as claimed in claim 1, wherein said backing is made of a transparent or translucent material.

11. The adhesive dressing as claimed in claim 2, wherein said backing is made of a transparent or translucent material.

12. The adhesive dressing as claimed in claim 1, wherein said backing is water-impermeable.

13. The adhesive dressing as claimed in claim 1, wherein said backing is made of resin.

14. The adhesive dressing as claimed in claim 2, wherein said backing is made of fabric.

15. The adhesive dressing as claimed in claim 2, wherein said backing is made of paper.

16. The adhesive dressing as claimed in claim 1, wherein said chemical composition serves as a pH indicator that changes in color to the extent that the color change is visible to the naked eye when said chemical composition varies from neutral to acidic.

17. The adhesive dressing as claimed in claim 2, wherein said chemical composition serves as a pH indicator that changes in color to the extent that the color change is visible to the naked eye when said chemical composition varies from neutral to acidic.

18. A adhesive dressing as claimed in claim 16, wherein the pH indicator changes in color to the extent that the color change is identifiable to the naked eye between acidic and neutral pHs.

19. The adhesive dressing as claimed in claim 17, wherein the pH indicator changes in color to the extent that the color change is identifiable to the naked eye between acidic and neutral pHs.

20. The adhesive dressing as claimed in claim 16, wherein the pH indicator includes at least on of the following: Indigo Carmine, Nile Blue, Methyl Red, Phenolphthalein, Congo Red, Bromcresol Green, Bromphenol Red, Bromthymol Blue, Cresol Red, Thymol Blue, Bromphenol Blue, Tetra-bromphenol Red, Bromcresol Purple, Alizarin Yellow, Aniline Blue, Litmus, Andrade, and Neutral Red.

21. The adhesive dressing as claimed in claim 17, wherein the pH indicator includes at least on of the following: Indigo Carmine, Nile Blue, Methyl Red, Phenolphthalein, Congo Red, Bromcresol Green, Bromphenol Red, Bromthymol Blue, Cresol Red, Thymol Blue, Bromphenol Blue, Tetra-bromphenol Red, Bromcresol Purple, Alizarin Yellow, Aniline Blue, Litmus, Andrade, and Neutral Red.

22. The adhesive dressing as claimed in claim 1, wherein said chemical composition serves as a hydrogen sulfide indicator that changes in color to the extent that the color change is visible to the naked eye when said chemical composition reacts with hydrogen sulfide.

23. The adhesive dressing as claimed in claim 7, wherein said chemical composition serves as a hydrogen sulfide indicator that changes in color to the extent that the color change is visible to the naked eye when said chemical composition reacts with hydrogen sulfide.

24. The adhesive dressing as claimed in claim 22, wherein the hydrogen sulfide indicator is at least one of lead acetate and a ferric ion.

25. The adhesive dressing as claimed in claim 23, wherein the hydrogen sulfide indicator is at least one of lead acetate and a ferric ion.

26. The adhesive dressing as claimed in claim 1, wherein said chemical composition comprises an auxiliary agent that is useful to cause said chemical composition to change in color.

27. The adhesive dressing as claimed in claim 2, wherein said chemical composition comprises an auxiliary agent that is useful to cause said chemical composition to change in color.

28. An adhesive dressing designed to be placed over a wound, comprising:
   a backing having a first surface and a second surface opposite the first surface;
   an adhesive layer provided around a periphery of the first surface of said backing to secure the adhesive dressing to the skin of a person or an animal with the first surface facing the skin; and
   a chemical composition incorporated in a keeper that is applied to a part of the first surface of said backing, said chemical composition changing in color to the extent that the color change is visible to the naked eye through said backing when bacteria grow in the wound,
   wherein the keeper has a circular hole.

* * * * *